(12) United States Patent
Matlock et al.

(10) Patent No.: US 10,967,159 B2
(45) Date of Patent: Apr. 6, 2021

(54) SINUPLASTY GUIDE WITH PLURALITY OF CONFIGURATIONS

(71) Applicant: Acclarent, Inc., Irvine, CA (US)

(72) Inventors: George L. Matlock, Pleasanton, CA (US); Don Q. Ngo-Chu, Irvine, CA (US); Jetmir Palushi, Irvine, CA (US); Tuan Pham, Huntington Beach, CA (US); Henry F. Salazar, Pico Rivera, CA (US); David A. Smith, Jr., Lake Forest, CA (US); John H. Thinnes, Jr., Mission Viejo, CA (US)

(73) Assignee: Acclarent, Inc., Irvine, CA (US)

( * ) Notice: Subject to any disclaimer, the term of this patent is extended or adjusted under 35 U.S.C. 154(b) by 232 days.

(21) Appl. No.: 16/009,297

(22) Filed: Jun. 15, 2018

(65) Prior Publication Data

US 2019/0060623 A1    Feb. 28, 2019

Related U.S. Application Data

(60) Provisional application No. 62/552,608, filed on Aug. 31, 2017.

(51) Int. Cl.
*A61M 29/02* (2006.01)
*A61B 17/24* (2006.01)
(Continued)

(52) U.S. Cl.
CPC .............. *A61M 29/02* (2013.01); *A61B 17/24* (2013.01); *A61B 17/3415* (2013.01);
(Continued)

(58) Field of Classification Search
CPC ........ A61M 2029/025; A61M 25/0021; A61M 25/0041; A61M 25/0662; A61M 25/0668;
(Continued)

(56) References Cited

U.S. PATENT DOCUMENTS 5,195,978 A * 3/1993 Schiffer ............ A61M 25/0169
                                                         604/161
9,155,492 B2   10/2015 Jenkins et al.
(Continued)

FOREIGN PATENT DOCUMENTS

EP       2 985 048 A1    2/2016

OTHER PUBLICATIONS

European Search Report and Written Opinion dated Feb. 12, 2019 for Application No. EP 18191695.8, 6 pgs.

*Primary Examiner* — Wade Miles
*Assistant Examiner* — Kankindi Rwego
(74) *Attorney, Agent, or Firm* — Frost Brown Todd LLC

(57) ABSTRACT

A catheter system and method of dilating first and second anatomies includes a guide catheter extending along a longitudinal axis that has a breakaway distal end portion with a conduit in communication with the lumen. The conduit is configured to guide a dilation catheter at a first predetermined angle relative to the longitudinal axis and a second predetermined angle relative to the longitudinal axis for respectively dilating the first and second anatomies. The breakaway distal end portion includes first and second guide segments at least partially defining the conduit and respectively extending the first and predetermined angles to first and second distal openings. The second guide segment is removably connected to the first guide segment for selectively guiding the dilation catheter along the second predetermined angle when connected and along the first predetermined angle when disconnected.

20 Claims, 6 Drawing Sheets

(51) Int. Cl.
  *A61B 17/34* (2006.01)
  *A61M 25/00* (2006.01)
  *A61B 17/00* (2006.01)
  *A61B 90/00* (2016.01)
  *A61M 25/10* (2013.01)
  *A61M 25/06* (2006.01)

(52) U.S. Cl.
  CPC ... *A61M 25/0041* (2013.01); *A61B 2017/003* (2013.01); *A61B 2017/00292* (2013.01); *A61B 2017/00331* (2013.01); *A61B 2017/00557* (2013.01); *A61B 2090/037* (2016.02); *A61M 25/0662* (2013.01); *A61M 25/10* (2013.01); *A61M 2029/025* (2013.01); *A61M 2210/0681* (2013.01)

(58) Field of Classification Search
  CPC .......... A61M 25/10; A61M 2025/0675; A61M 2025/0681; A61M 2025/0687; A61B 17/3415; A61B 17/3417; A61B 17/3419; A61B 17/3421; A61B 2017/3443; A61B 2017/3454; A61B 1/00101; A61F 2/95; A61F 2/954; A61F 2/958; A61F 2/962; A61F 2002/9528; A61F 2002/9534
  See application file for complete search history.

(56) References Cited

U.S. PATENT DOCUMENTS

| | | | |
|---|---|---|---|
| 9,962,530 | B2 | 5/2018 | Johnson et al. |
| 2007/0032850 | A1* | 2/2007 | Ruiz ................... A61F 2/2412 623/1.11 |
| 2008/0183128 | A1 | 7/2008 | Morriss et al. |
| 2010/0030031 | A1 | 2/2010 | Goldfarb et al. |
| 2010/0211156 | A1* | 8/2010 | Linder ................... A61F 2/013 623/1.11 |
| 2011/0004057 | A1 | 1/2011 | Goldfarb et al. |
| 2012/0071856 | A1* | 3/2012 | Goldfarb ............... A61B 17/24 604/514 |
| 2012/0071857 | A1 | 3/2012 | Goldfarb et al. |
| 2012/0323069 | A1* | 12/2012 | Stout ..................... A61B 1/303 600/104 |
| 2013/0053825 | A1* | 2/2013 | Moulton ........... A61M 25/0074 604/523 |
| 2016/0310714 | A1 | 10/2016 | Jenkins et al. |
| 2017/0120020 | A1 | 5/2017 | Lin et al. |

* cited by examiner

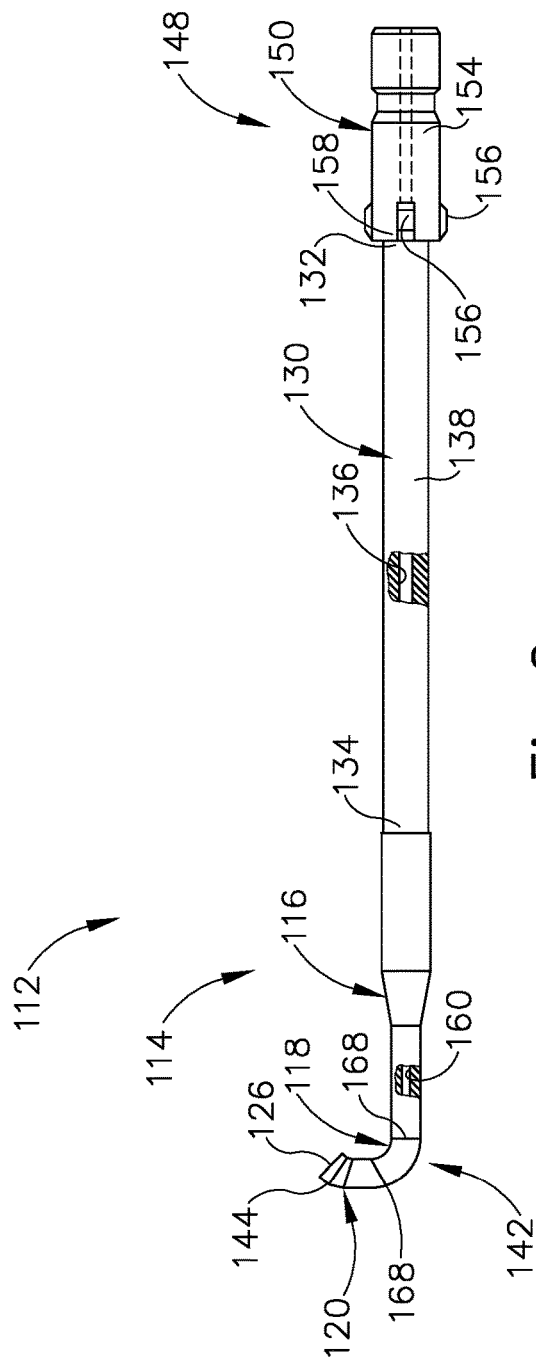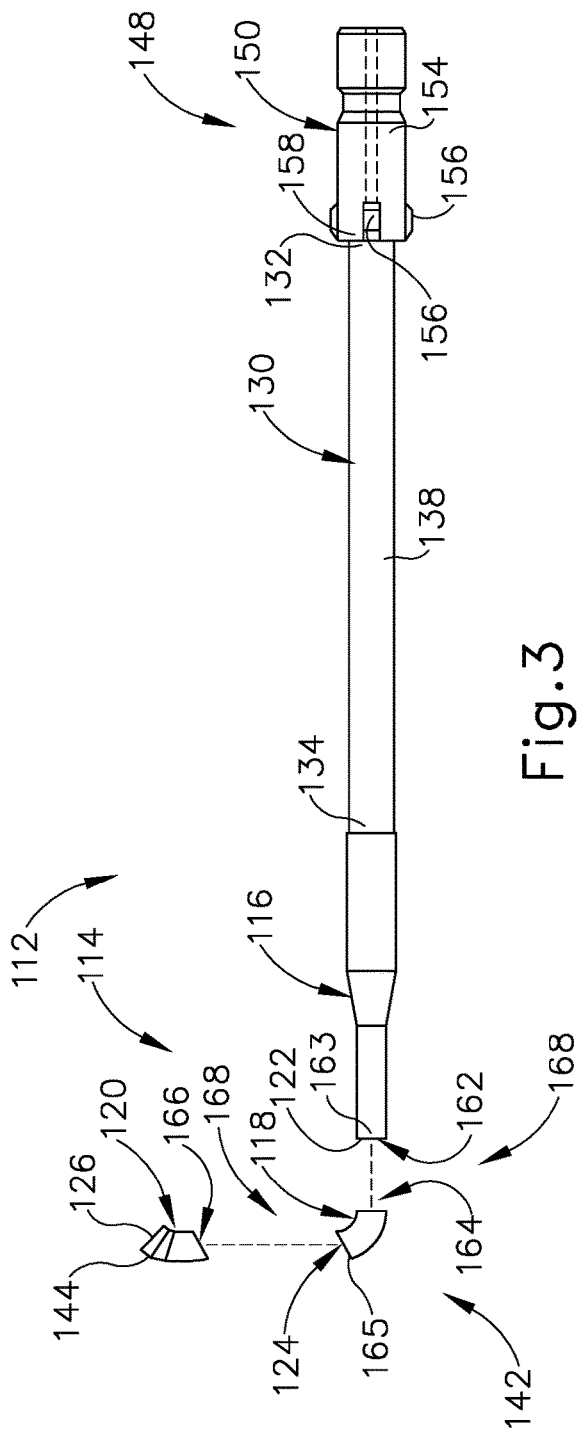

SINUPLASTY GUIDE WITH PLURALITY OF CONFIGURATIONS

PRIORITY

This application claims priority to U.S. Provisional Patent Application Ser. No. 62/552,608, filed Aug. 31, 2017, entitled "Sinuplasty Guide with Plurality Of Configurations," the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry™ Sinus Illumination System by Acclarent, Inc. of Irvine, Calif.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a side elevational view of a first exemplary breakaway guide catheter for use with the dilation instrument assembly of FIG. 1A;

FIG. 3 depicts a partially exploded side elevation view of the breakaway guide catheter of FIG. 2;

Figure 1A:
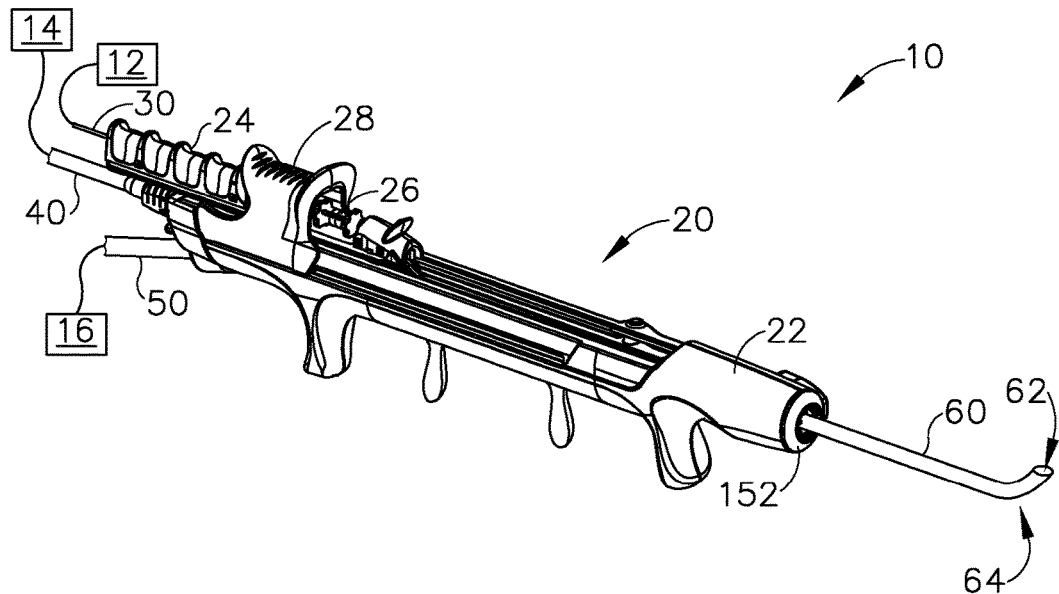
FIG. 1A depicts a perspective view of an exemplary dilation instrument assembly, with an exemplary guidewire in a proximal position, and with a dilation catheter in a proximal position.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIGS. 1A-1D shows a first exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20). In some versions, guidewire power source (12) is part of an IGS system as described below with respect to FIGS. 2-3. In some other versions, guidewire power source (12) comprises a source of light as described below with respect to FIGS. 4-6. In the present example shown in FIGS. 1A-1D, inflation source (14) comprises a source of saline. However, it should be understood that any other suitable source of fluid (liquid or otherwise) may be used. Also in the present example, irrigation fluid source (16) comprises a source of saline. Again, though, any other suitable source of fluid may be used. It should also be understood that flush fluid source (16) may be omitted in some versions.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22). It should therefore be understood that dilation instrument (20) may be fully operated by a single hand of a human operator.

A. Exemplary Guide Catheter

A guide catheter (60) extends distally from handle body (22). Guide catheter (60) includes an open distal end (62) and a bend (64) formed proximal to open distal end (62). In the present example, dilation instrument (20) is configured to removably receive several different kinds of guide catheters (60), each guide catheter (60) having a different angle formed by bend (64). These different angles may facilitate access to different anatomical structures. Various examples of angles and associated anatomical structures are described in one or more of the references cited herein; while further examples will be apparent to those of ordinary skill in the art in view of the teachings herein. Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

B. Exemplary Guidewire

Figure 1B:
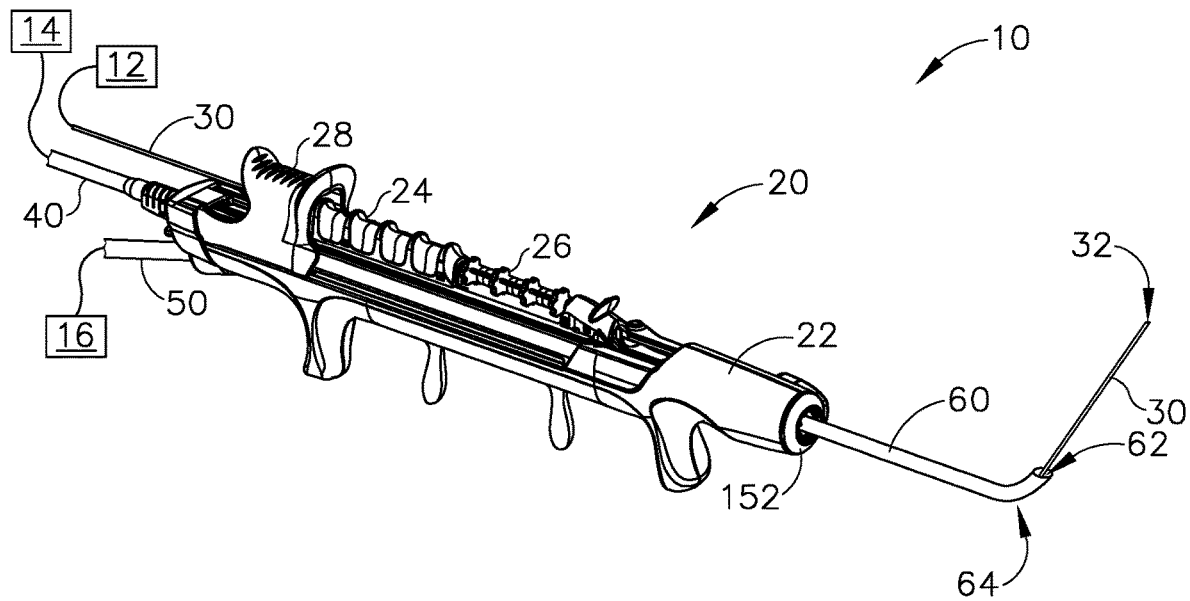
FIG. 1B depicts a perspective view of the dilation instrument assembly of FIG. 1A, with the guidewire in a distal position, and with the dilation catheter in the proximal position.

Dilation instrument (30) further comprises an exemplary guidewire (30), which is coaxially disposed in guide catheter (60). Guidewire slider (24) is secured to guidewire (30) such that translation of guidewire slider (24) relative to handle body (22) provides corresponding translation of guidewire (30) relative to handle body (22). In particular, translation of guidewire slider (24) from a proximal position (FIG. 1A) to a distal position (FIG. 1B) causes corresponding translation of guidewire (30) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

In some versions, guidewire (30) includes a preformed bend formed just proximal to a distal end (32) of guidewire (30). In such versions, the preformed bend and the rotatability provided via guidewire spinner (26) may facilitate alignment and insertion of distal end (32) into a sinus ostium, Eustachian tube, or other passageway to be dilated. Also in some versions, guidewire (30) includes at least one optical fiber extending to a lens or other optically transmissive feature in distal end (32), such as illuminating guidewire (150) (see FIGS. 4-6) discussed below. Optical fiber may be in optical communication with guidewire power source (12), such that light may be communicated from guidewire power source (12) to distal end (32). In such versions, guidewire (30) may provide transillumination through a patient's skin in order to provide visual feedback to the operator indicating that distal end (32) has reached a targeted anatomical structure.

By way of example only, guidewire (30) may be configured in accordance with at least some of the teachings of U.S. Pat. No. 9,155,492, the disclosure of which is incorporated by reference herein. In some versions, guidewire (30) is configured similar to the Relieva Luma Sentry™

Sinus Illumination System by Acclarent, Inc. of Irvine, Calif. In addition to, or as an alternative to, including one or more optical fibers, guidewire (30) may include a sensor and at least one wire that enables guidewire (30) to provide compatibility with an IGS system as described in greater detail below. Other features and operabilities that may be incorporated into guidewire (30) will be apparent to those of ordinary skill in the art in view of the teachings herein.

C. Exemplary Dilation Catheter

Figure 1C:
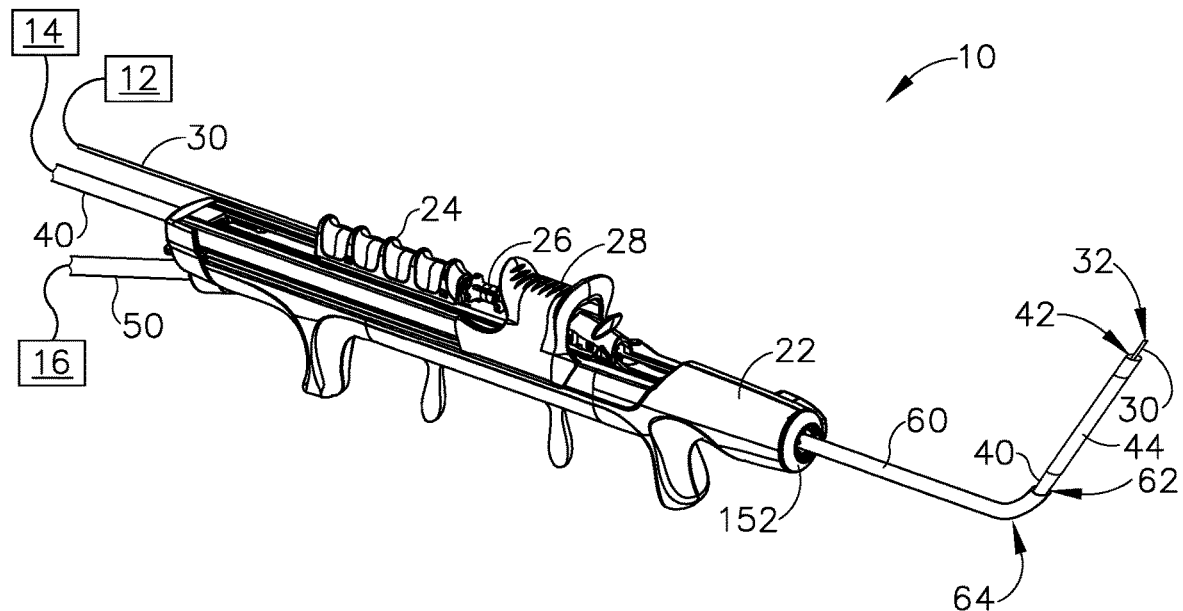
FIG. 1C depicts a perspective view of the dilation instrument assembly of FIG. 1A, with the guidewire in a distal position, with the dilation catheter in a distal position, and with a dilator of the dilation catheter in a non-dilated state.

Dilation instrument (30) further comprises a dilation catheter (40), which is coaxially disposed in guide catheter (60). Dilation catheter slider (28) is secured to dilation catheter (40) such that translation of dilation catheter slider (28) relative to handle body (22) provides corresponding translation of dilation catheter (40) relative to handle body (22). In particular, translation of dilation catheter slider (28) from a proximal position (FIG. 1B) to a distal position (FIG. 1C) causes corresponding translation of dilation catheter (40) from a proximal position (FIG. 1B) to a distal position (FIG. 1C). When dilation catheter (40) is in a distal position, a distal portion of dilation catheter (40) protrudes distally from open distal end (62) of guide catheter (60). As can also be seen in FIG. 1C, a distal portion of guidewire (30) protrudes distally from the open distal end of dilation catheter (40) when guidewire (30) and dilation catheter are both in distal positions.

Figure 1D:
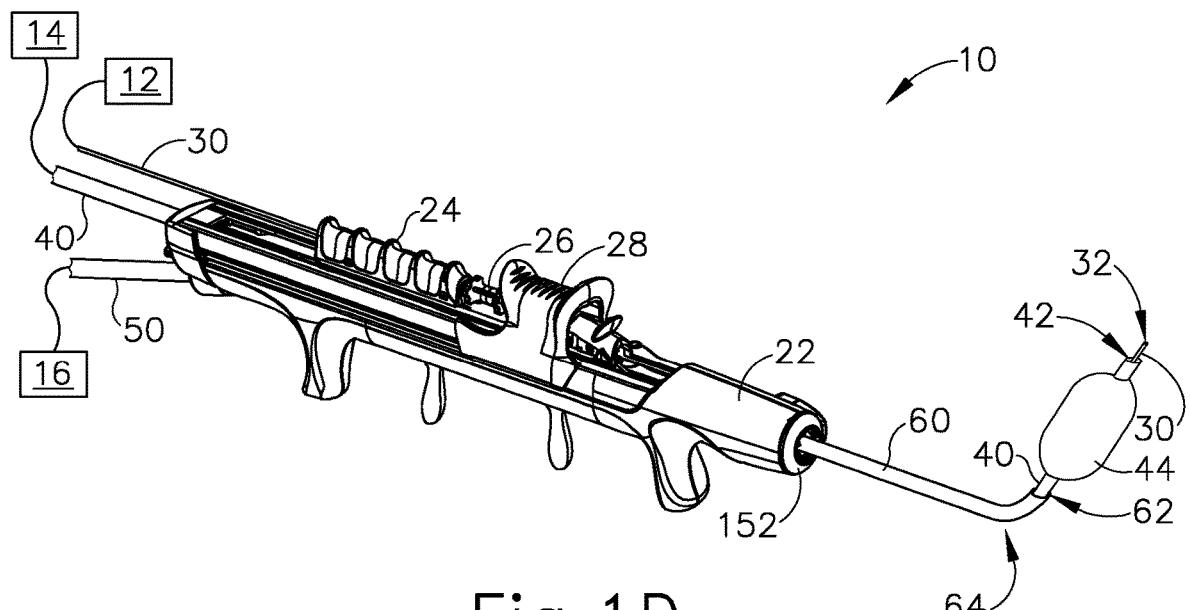
FIG. 1D depicts a perspective view of the dilation instrument assembly of FIG. 1A, with the guidewire in a distal position, with the dilation catheter in the distal position, and with a dilator of the dilation catheter in a dilated state.

Dilation catheter (40) of the present example comprises a non-extensible balloon (44) located just proximal to an open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In some versions, inflation source (14) comprises a manually actuated source of pressurized fluid. In some such versions, the manually actuated source of pressurized fluid is configured and operable in accordance with at least some of the teachings of U.S. Pat. No. 9,962,530, entitled "Inflator for Dilation of Anatomical Passageway," issued May 8, 2018, the disclosure of which is incorporated by reference herein. Other suitable configurations that may be used to provide a source of pressurized fluid will be apparent to those of ordinary skill in the art in view of the teachings herein.

While not shown, it should be understood that dilation catheter (40) may include at least two separate lumens that are in fluid isolation relative to each other. One lumen may provide a path for fluid communication between balloon (44) and inflation source (14). The other lumen may provide a path to slidably receive guidewire (30).

While dilation catheter (40) of the present example is configured to transition between a non-dilated state and a dilated state based on the communication of fluid to and from balloon (44), it should be understood that dilation catheter (40) may include various other kinds of structures to serve as a dilator. By way of example only, balloon (44) may be replaced with a mechanical dilator in some other versions. Dilation catheter (40) may be constructed and operable in accordance with any of the various references cited herein. In some versions, dilator catheter (40) is configured and operable similar to the Relieva Ultirra™ Sinus Balloon Catheter by Acclarent, Inc. of Irvine, Calif. In some other versions, dilator catheter (40) is configured and operable similar to the Relieva Solo Pro™ Sinus Balloon Catheter by Acclarent, Inc. of Irvine, Calif. Other suitable variations of dilation catheter (40) will be apparent to those of ordinary skill in the art in view of the teachings herein.

D. Exemplary Irrigation Features

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after the dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via tube (50), to enable irrigation of the anatomical site in the patient. An example of an irrigation catheter that may be fed through guide catheter (60) to reach the irrigation site after removal of dilation catheter (60) is the Relieva Vortex® Sinus Irrigation Catheter by Acclarent, Inc. of Irvine, Calif. Another example of an irrigation catheter that may be fed through guide catheter (60) to reach the irrigation site after removal of dilation catheter (40) is the Relieva Ultirra® Sinus Irrigation Catheter by Acclarent, Inc. of Irvine, Calif.

In some other versions, dilation catheter (40) includes an additional irrigation lumen and an associated set of irrigation ports near distal end (42), such that dilation catheter (40) may be coupled with irrigation fluid source (16) via tube (50). Thus, a separate, dedicated irrigation catheter is not necessarily required in order to provide irrigation.

By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," issued Dec. 8, 2009, now abandoned, the disclosure of which is incorporated by reference herein. Of course, irrigation may be provided in the absence of a dilation procedure; and a dilation procedure may be completed without also including irrigation. It should therefore be understood that dilation fluid source (16) and tube (50) are merely optional.

E. Exemplary Variations

In the present example, guidewire (30) is coaxially disposed within dilation catheter (40), which is coaxially disposed within guide catheter (60). In some other versions, guide catheter (60) is omitted from dilation instrument (20). In some such versions, a malleable guide catheter is used to guide guidewire (30) and dilation catheter (40). In some such versions, guidewire (30) is omitted and dilation catheter (40) is slidably disposed about the exterior of the internal malleable guide catheter. In some other versions, guidewire (30) is slidably disposed about the exterior of the internal malleable guide catheter; and dilation catheter (40) is slidably disposed about the exterior of guidewire (30). In still other versions, guidewire (30) is slidably disposed within the interior of the malleable guide catheter; and dilation catheter (40) is slidably disposed about the exterior of the malleable guide catheter.

By way of example only, versions of dilation instrument (20) that include a malleable guide catheter may be constructed and operable in accordance with at least some of the teachings of U.S. Pub. No. 2016/0310714, entitled "Balloon Dilation System with Malleable Internal Guide," published Oct. 27, 2016, issued as U.S. Pat. No. 10,137,285 on Nov. 27, 2018, the disclosure of which is incorporated by reference herein. As another merely illustrative example, versions of dilation instrument (20) that include a malleable guide catheter may be constructed and operable in accordance with at least some of the teachings of U.S. Pub. No. 2017/0120020, entitled "Apparatus for Bending Malleable Guide of Surgical Instrument," published May 5, 2017, issued as U.S. Pat. No. 10,137,286 on Nov. 27, 2018, the disclosure of which is incorporated by reference herein; and/or U.S. Pub. No. 2012/0071857, entitled "Methods and Apparatus for Treating Disorders of the Sinuses," published Mar. 22, 2012, now abandoned, the disclosure of which is incorporated by reference herein.

II. Exemplary Breakaway Guide Catheter

As noted above, it may be desirable to enable use of dilation instrument assembly (10) to dilate various different anatomical passageways (e.g., frontal sinus ostium, frontal recess, maxillary sinus ostium, sphenoid sinus ostium, ethmoid sinus ostium, Eustachian tube, etc.). In the example of guide catheter (60), the operator must remove and replace guide catheter (60) in order to achieve different exit angles for dilation catheter (40), to thereby facilitate dilation of different anatomical passageways within a patient's head. It may be desirable to enable the operator to more readily achieve different exit angles for dilation catheter (40), to thereby facilitate dilation of different anatomical passageways within a patient's head, without requiring the operator to remove and replace guide catheter (60). To that end, FIGS. 2-3 show a first exemplary breakaway guide catheter (112) that may be used in place of a series of guide catheters (60) for successively dilating various different anatomical passageways.

Breakaway guide catheter (112) of the present example has a breakaway distal portion (114) that includes a plurality of guide segments (116, 118, 120) removably connected together. Each guide segment (116, 118, 120) distally terminates at a respective distal opening (122, 124, 126) therein such that removal of a distal-most guide segment, such as guide segment (120), shortens breakaway distal portion (114) and reveals a new distal-most opening, such as distal opening (124). Guide segments (116, 118, 120), alone or collectively, extend respectively at predetermined angles to distal openings (122, 124, 126) to thereby dilate various different anatomical passageways in succession with each removal of the remaining, distal-most guide segment. Such "predetermined angles" may also be referred to herein as "predefined angles."

In addition to breakaway distal portion (114), breakaway guide catheter (112) of the present example further includes an elongate tubular shaft (130) that has a proximal end (132), a distal end (134), and a lumen (136) therebetween. Elongate tubular shaft (130) distally extends along a longitudinal axis (137) (see FIG. 8A) to breakaway distal portion (114) of breakaway guide catheter (112) having at least one guide segment (116, 118, 120) for dilating anatomical passageways as discussed below in greater detail. To this end, breakaway guide catheter (112) may have any suitable length, diameter, angle of bend, and location of the bend along the length of breakaway guide catheter (112), to facilitate accessing the plurality of desired anatomies. By way of example only, breakaway guide catheter (112) may have a length between approximately 8 cm and approximately 20 cm, and more particularly between approximately 10 cm and approximately 15 cm, and in particular approximately 11 cm. Alternatively, any other suitable dimensions may be used.

Elongate tubular shaft (130) has an outer shaft tube (138), an inner shaft tube (not shown), and lumen (136) therein. Outer shaft tube (138) may be constructed of a stiff material such as stainless steel and inner shaft tube (not shown) may be constructed of a more flexible material such as a polymeric material including but not limited to nylon and further including a PTFE liner. By way of example only, lumen (136) may have a diameter of between approximately 2 mm and 3 mm, and particularly between approximately 2.5 mm and 2.6 mm such that dilation catheter (40) (see FIG. 1D) can be easily inserted into lumen (136). Alternatively, any other suitable dimensions may be used.

The combination breakaway guide catheter (112) and dilation catheter (40) make a compact system that is designed for a one-handed procedure. By way of example only, the length of breakaway guide catheter (112) that is distal of a preformed bend (142) in the breakaway guide catheter (112) may be between approximately 0.5 cm and 2.0 cm, or more particularly between approximately 1 and 2 cm, and in particular approximately 1 cm. This compactness may help reduce interference with other instruments, such as an endoscope (not shown) that may be used to help in visualizing the positioning of the system. Again, though, any other suitable dimensions may be used.

By way of example, breakaway distal portion (114) of breakaway guide catheter (112) has preformed bend (142) with a predetermined collective angle between approximately 105 degrees and approximately 115 degrees, and more particularly approximately 110 degrees to facilitate access into a maxillary sinus ostium. Breakaway distal portion (114) of breakaway guide catheter (112) may be constructed of a transparent material such as a polymer including but not limited to nylon, such that dilation catheter (40) (see FIG. 1D) is visible within breakaway distal portion (114) and more flexible than elongate tubular shaft (130). In one example, a distal tip (144) of breakaway distal portion (114) is made of polyether block amides (e.g., PEBAX® by Arkema) such that it provides for atraumatic access to the maxillary sinus ostium, and may contain 20% barium sulfate or other similar radiopaque materials for visualizable access. By way of further example only, distal portion (114) may be formed of stainless steel or Ultem™ by Saudi Basic Industries Corporation of Houston, Tex.

Figure 7A:
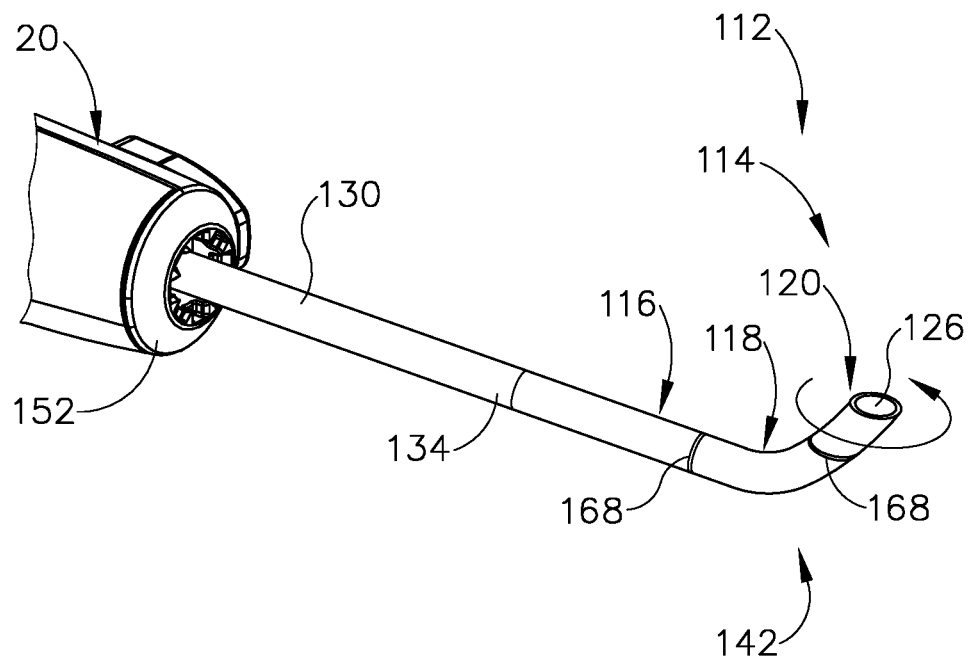
FIG. 7A depicts an enlarged perspective view of the breakaway guide catheter of FIG. 2 operatively connected to the dilation instrument assembly of FIG. 1A and a portion of the breakaway guide catheter being removed therefrom.

A proximal portion (148) of breakaway guide catheter (112) includes a hub (150) configured to be received within a guide port (152) of handle body (22) (see FIG. 7A) of instrument assembly (10) (see FIG. 7A). Hub (150) has a hub body (154) and a plurality of ribs (156) angularly positioned thereabout that are collectively configured to be received and secured within guide port (152) (see FIG. 7A). Hub (150) is inserted into guide port (152) (see FIG. 7A) until a distal, annular shoulder (158) abuts against an engagement surface (not shown) of guide port (152). Hub (150) is ergonomically designed for insertion, location, and rotation with slight manipulations using a single hand.

With respect to FIGS. 2-3, the present example of breakaway distal portion (114) of breakaway guide catheter (112) includes a conduit (160) defined by guide segments (116, 118, 120). Guide segments (116, 118, 120) are more particularly referred to herein as a proximal guide segment (116), an intermediate guide segment (118), and a distal guide segment (120). It will be appreciated that alternative positions, angles, and numbers of such guide segments may vary in accordance with the invention described herein. The invention is thus not intended to be unnecessarily limited to proximal, intermediate, and distal guide segments (116, 118, 120) described herein.

Proximal guide segment (116) is rigidly connected to distal end (134) of elongate tubular shaft (130) and has a predetermined proximal angle of between approximately −5 degrees and approximately 5 degrees, and more particularly approximately 0 degrees, relative to longitudinal axis (137) (see FIG. 8A) of elongate tubular shaft (130). Proximal guide segment (116) further defines a proximal bore (162) extending along the predetermined proximal angle to distal opening (122) of proximal guide segment (116). Distal opening (122) of proximal guide segment (116) is thus positioned at the predetermined proximal angle relative to longitudinal axis (137) (see FIG. 8A) and, in the present example, is generally aligned with longitudinal axis (137) (see FIG. 8A). A distal tip (163) of proximal guide segment (116) surrounds distal opening (122) and may be atraumatic and/or radiopaque similar to distal tip (144) discussed above.

Intermediate guide segment (118) is removably connected to proximal guide segment (116). Collectively, intermediate and proximal guide segments (118, 116) thus have a predetermined intermediate angle of between approximately 50 degrees and approximately 60 degrees, and more particularly approximately 55 degrees, relative to longitudinal axis (137) (see FIG. 8A) of elongate tubular shaft (130). Intermediate guide segment (118) further defines an intermediate bore (164) extending along the predetermined intermediate angle to distal opening (124) of intermediate guide segment (118). Distal opening (124) of intermediate guide segment (118) is thus positioned at the predetermined intermediate angle relative to longitudinal axis (137) (see FIG. 8A) and, in the present example, is offset from longitudinal axis (137) (see FIG. 8A). A distal tip (165) of intermediate guide segment (118) surrounds distal opening (124) and may be atraumatic and/or radiopaque similar to distal tip (144) discussed above.

Distal guide segment (120) is removably connected to intermediate guide segment (118). Collectively, distal, intermediate, and proximal guide segments (120, 118, 116) thus have a predetermined distal angle of between approximately 105 degrees and approximately 110 degrees, and more particularly approximately 115 degrees, relative to longitudinal axis (137) (see FIG. 8A) of elongate tubular shaft (130). Distal guide segment (118) further defines a distal bore (166) extending along the predetermined distal angle to distal opening (126) of distal guide segment (120). Distal opening (126) of intermediate guide segment (118) is thus positioned at the predetermined intermediate angle relative to longitudinal axis (137) (see FIG. 8A) and, in the present example, is generally offset from longitudinal axis (137) (see FIG. 8A). Distal opening (126) is also surrounded by distal tip (144) of distal guide segment (122). In the present example, the predetermined collective angle is the same angle as the predetermined distal angle.

Figure 4:
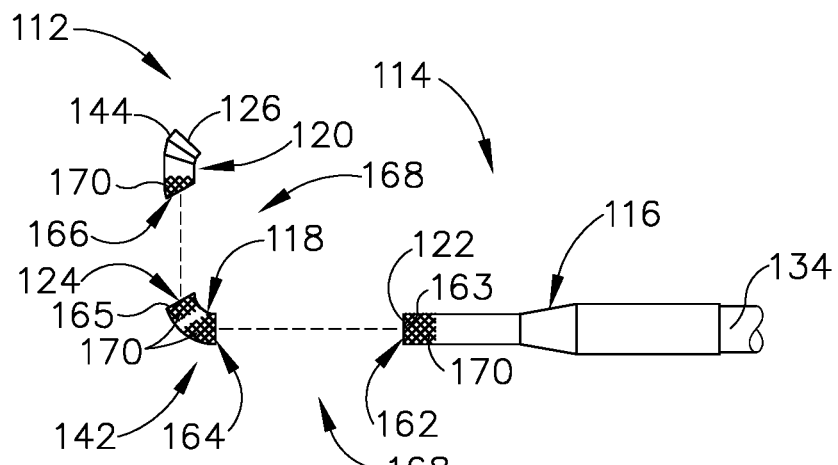
FIG. 4 depicts an enlarged partially exploded side elevation view of the breakaway guide catheter of FIG. 2.

Intermediate guide segment (118) is removably connected between each of distal guide segment (120) and proximal guide segment (116) by a pair of respective breakaway couplings (168) having a proximal coupling portion and a distal coupling portion. FIG. 4 shows breakaway coupling (168) as a frangible coupling (168) with proximal and distal coupling portions including a frangible lattice web (170) configured to provide tensile and column strength thereabong. More particularly, one frangible lattice web (170) extends between each of distal and intermediate guide segments (120, 118), while another frangible lattice web (170) extends between each of proximal and intermediate guide segments (116, 118). Each frangible coupling (168) is configured to break upon application of a predetermined torque. In one example, frangible coupling (168) is configured to weaken upon exposure to at least one of heat or moisture, such as the heat or moisture present within the patient. In another example, frangible coupling (168) is scored or perforated for further weakening to the predetermined torque.

Figure 5:
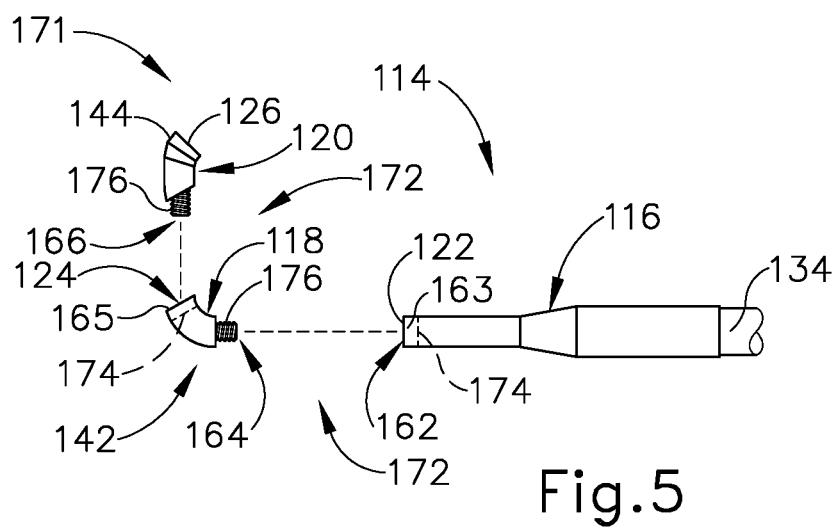
FIG. 5 depicts an enlarged partially exploded side elevation view of a second exemplary breakaway guide catheter.
Figure 6:
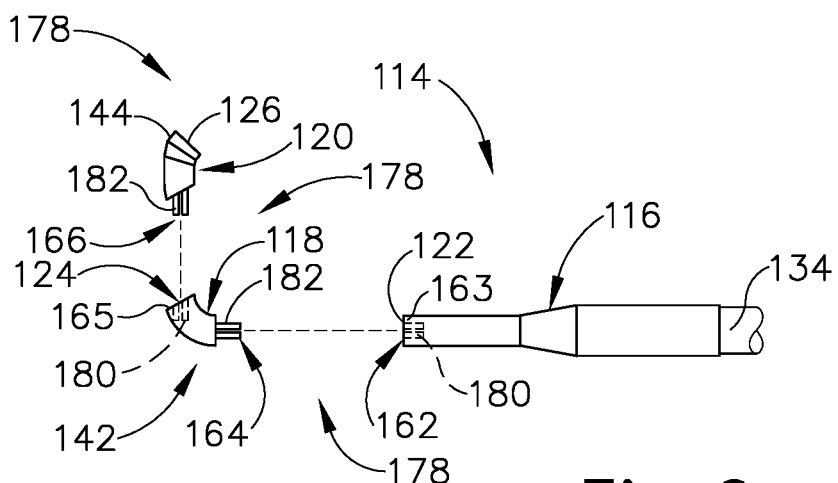
FIG. 6 depicts an enlarged partially exploded side elevation view of a third exemplary breakaway guide catheter.

FIG. 5 shows a second exemplary breakaway guide catheter (171) with an alternative breakaway coupling (172) as a threaded coupling (172). Threaded coupling (172) has a proximal coupling portion including a threaded hole (174) and a distal coupling portion including a threaded stud (176). Each threaded stud (176) is threadedably received within each respective threaded hole (174) and configured to be rotatably loosened and disconnected upon application of a predetermined torque. FIG. 6 shows a third exemplary breakaway guide catheter (177) with another alternative breakaway coupling (178) as a slide coupling (178). Slide coupling (178) has a proximal coupling portion including a slot (180) and a distal coupling portion including a longitudinal rail (182). Each longitudinal rail (182) is received within each respective slot (180) as cooperating detents and configured to be longitudinally separated upon application of a predetermined force. While the above breakaway couplings (168, 172, 178) includes various structures for connection and/or weakening, it will be appreciated that such structures may be used in any combination, in whole in or part. For example, one such removable connection may be between distal and intermediate guide segments (120, 118), while another such removable connection may be between proximal and intermediate guide segments (116, 118). The invention is thus not intended to be unnecessarily limited to the particular breakaway couplings (168, 172, 178) described herein.

Figure 8A:
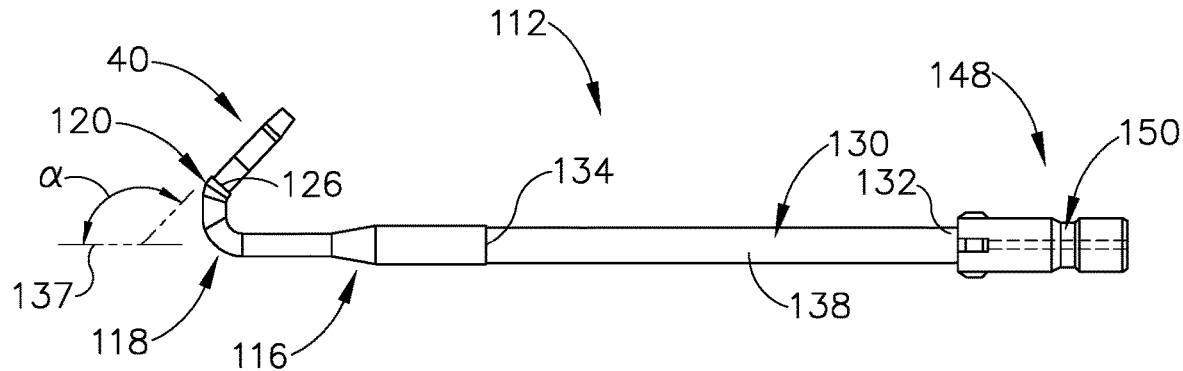
FIG. 8A depicts a side elevation view of the guide catheter of FIG. 2 guiding the dilation catheter of FIG. 1A at a first predetermined angle.

In use, with respect to FIGS. 7A and 8A, breakaway guide catheter (112) is received within guide port (152) of dilation instrument (20), and dilation catheter (40) inserts through breakaway guide catheter (112) to extend distally from distal opening (126). Each of proximal, intermediate, and distal guide segments (116, 118, 120) collectively guides dilation catheter (40) to the predetermined distal angle of approximately 110 degrees for accessing and dilating the maxillary sinus ostium with balloon (44) (see FIG. 1D). Once the maxillary sinus ostium is dilated, the clinician removes the distal-most, distal guide segment (120), such as by twisting frangible coupling (168) with the predetermined torque and breaking frangible coupling (168). Removing distal guide segment (120) reveals distal opening (124) of intermediate guide segment (118) as the distal-most remaining opening (124).

Figure 7B:
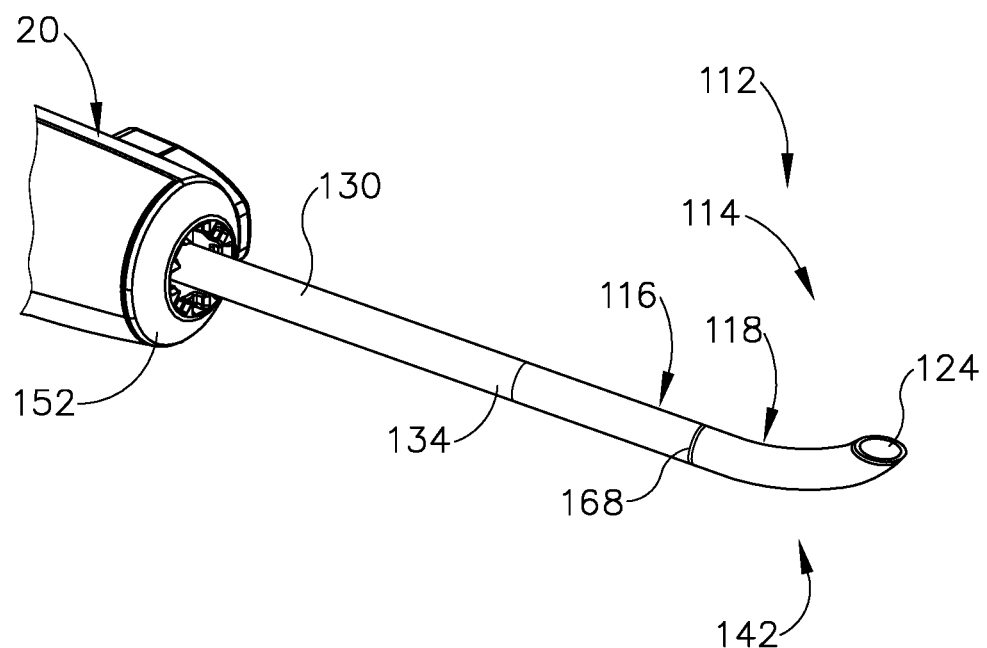
FIG. 7B depicts the enlarged perspective view of the breakaway guide catheter and the dilation instrument assembly similar to FIG. 7A, but showing the portion of the breakaway guide catheter removed therefrom.
Figure 8B:
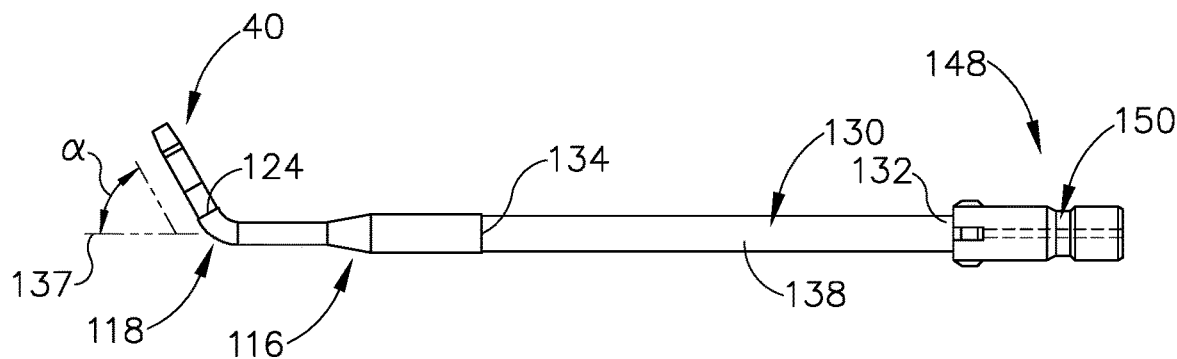
FIG. 8B depicts a side elevation view of the guide catheter of FIG. 2 guiding the dilation catheter of FIG. 1A at a second predetermined angle.

The clinician discards distal guide segment (120) as shown in FIG. 7B and continues with breakaway guide catheter (112) having intermediate and proximal guide segments (116, 118), but without distal guide segment (120) as shown in FIG. 8B. Each of remaining proximal and intermediate guide segments (116, 118) collectively guides dilation catheter (40) to the predetermined distal angle of approximately 55 degrees for accessing and dilating the frontal recess with balloon (44) (see FIG. 1D). Once the frontal recess is dilated, the clinician removes the distal-most remaining, intermediate guide segment (118), such as by twisting frangible coupling (168) with the predetermined torque and breaking frangible coupling (168). Removing intermediate segment (118) reveals distal opening (122) of proximal guide segment (116) as the distal-most remaining opening (122).

Figure 8C:
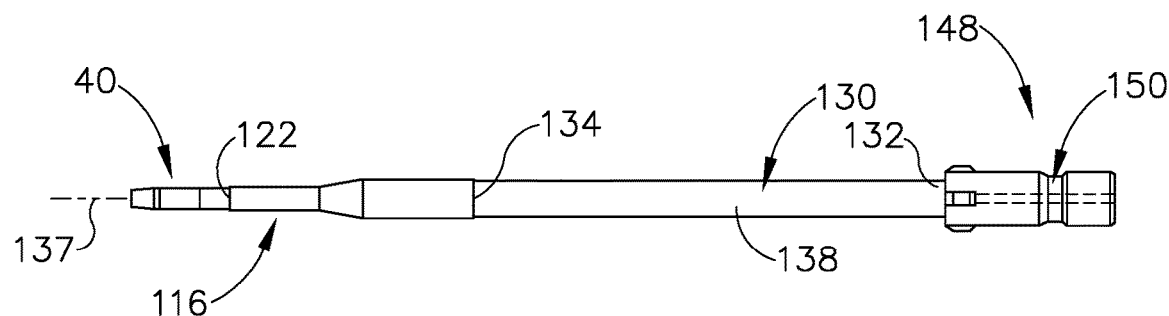
FIG. 8C depicts a side elevation view of the guide catheter of FIG. 2 guiding the dilation catheter of FIG. 1A at a third predetermined angle.

The clinician discards intermediate guide segment (118) similar to distal guide segment (120) shown in FIG. 7B and continues with breakaway guide catheter (112) having proximal guide segment (116), but without distal guide segment (120) and intermediate guide segment (118) as shown in FIG. 8C. Remaining proximal guide segment (116) guides dilation catheter (40) to the predetermined distal angle of approximately 0 degrees for accessing and dilating the sphenoid sinus ostium with balloon (44) (see FIG. 1D). Once the sphenoid sinus ostium is dilated, the clinician removes the remaining portion of breakaway guide catheter (112) from dilation instrument (20) (see FIG. 7A) to be discarded. While the above description provides the use of breakaway guide catheter (112) for successive dilation of the maxillary sinus ostium, the frontal recess, and the sphenoid sinus ostium as well as removal of guide segments (118, 120), it will be appreciated that alternative anatomies or combinations of guide segments (116, 118, 120) may be used. The invention is thus not intended to be unnecessarily limited to successive use with the maxillary sinus ostium, the frontal recess, and the sphenoid sinus ostium as described herein.

In view of the foregoing, the clinician may readily achieve various exit angles for dilation catheter (40) and/or guidewire (30) by removing one or more guide segments (118, 120). Thus, the clinician may readily dilate various anatomical passageways without having to exchange instruments; and without having to replace pieces of dilation instrument assembly (10). In some versions, one or more portions of guide catheter (112) includes/include markings indicating a particular anatomical passageway associated with different guide segments (116, 118, 120) of breakaway distal portion (114). Thus, when the clinician wishes to dilate a particular anatomical passageway, the operator may observe such markings, until the markings indicate that guide segments (116, 118, 120) are associated with the targeted anatomical passageway.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A catheter system, comprising: (a) a body; (b) a dilation catheter extending distally from the body and including an expandable dilator; and (c) a guide catheter including: (i) a shaft extending distally from the body and having a lumen extending longitudinally along a longitudinal axis, wherein the lumen movably receives the dilation catheter therein, and (ii) a breakaway distal end portion having a conduit in communication with the lumen, wherein the conduit distally projects from the shaft and is configured to guide the dilation catheter at a first predetermined angle relative to the longitudinal axis and a second predetermined angle relative to the longitudinal axis for respectively dilating a first anatomy and a second anatomy, wherein the breakaway distal end portion includes: (A) a first guide segment at least partially defining the conduit and distally extending at the first predetermined angle to a first distal opening, and (B) a second guide segment at least partially defining the conduit and distally extending from the first guide segment at the second predetermined angle to a second distal opening, wherein the second guide segment is removably connected to the first guide segment, wherein the first guide segment connected to the second guide segment are collectively configured to guide the dilation catheter through the second distal opening at the second predetermined angle for dilating the second anatomy, and wherein the first guide segment selectively disconnected from the second guide segment is configured to guide the dilation catheter through the first distal opening at the first predetermined angle for dilating the first anatomy.

Example 2

The catheter system of Example 1, wherein the conduit of the breakaway distal end portion is further configured to guide the dilation catheter at a third predetermined angle relative to the longitudinal axis for respectively dilating a third anatomy, and wherein the breakaway distal end portion further includes a third guide segment at least partially defining the conduit and distally extending from the second guide segment at the third predetermined angle to a third distal opening, wherein the third guide segment is removably connected to the second guide segment, and wherein the second guide segment connected to the third guide segment are collectively configured to guide the dilation catheter through the third distal opening at the third predetermined angle for dilating the third anatomy.

Example 3

The catheter system of Example 2, wherein the third, second, and first guide segments connected together are configured to guide the dilation catheter through the third distal opening at the third predetermined angle to dilate the third anatomy, wherein the third predetermined angle is between approximately 105 degrees and approximately 115 degrees, and wherein the third anatomy is a maxillary sinus ostium.

Example 4

The catheter system of Example 3, wherein the second and first guide segments connected together are configured to guide the dilation catheter through the second distal opening at the second predetermined angle to dilate the second anatomy, wherein the second predetermined angle is between approximately 50 degrees and approximately 60 degrees, and wherein the second anatomy is a frontal recess.

Example 5

The catheter system of Example 4, wherein the first guide segment is configured to guide the dilation catheter through the first distal opening at the first predetermined angle to dilate the first anatomy, wherein the first predetermined angle is approximately 0 degrees, and wherein the first anatomy is a sphenoid sinus ostium.

Example 6

The catheter system of any one or more of Examples 1 through 5, wherein the second and first guide segments connected together are configured to guide the dilation catheter through the second distal opening at the second predetermined angle to dilate the second anatomy, wherein the second predetermined angle is between approximately 105 degrees and approximately 115 degrees, and wherein the second anatomy is a maxillary sinus ostium.

Example 7

The catheter system of Example 6, wherein the first guide segment is configured to guide the dilation catheter through the first distal opening at the first predetermined angle to dilate the first anatomy, wherein the first predetermined angle is between approximately 50 degrees and approximately 60 degrees, and wherein the first anatomy is a frontal recess.

Example 8

The catheter system of any one or more of Examples 1 through 7, wherein the second and first guide segments connected together are configured to guide the dilation catheter through the second distal opening at the second predetermined angle to dilate the second anatomy, wherein the second predetermined angle is between approximately 50 degrees and approximately 60 degrees, and wherein the second anatomy is a frontal recess.

Example 9

The catheter system of Example 8, wherein the first guide segment is configured to guide the dilation catheter through the first distal opening at the first predetermined angle to dilate the first anatomy, wherein the first predetermined angle is approximately 0 degrees, and wherein the first anatomy is a sphenoid sinus ostium.

Example 10

The catheter system of any one or more of Examples 1 through 9, wherein the first guide segment is removably connected to the second guide segment by a frangible coupling for selective removal of the second guide segment from the first guide segment.

Example 11

The catheter system of Example 10, wherein the frangible coupling is configured to weaken upon exposure to at least one of heat or moisture.

Example 12

The catheter system of any one or more of Examples 10 through 11, wherein the frangible coupling includes a scored portion.

Example 13

The catheter system of any one or more of Examples 10 through 12, wherein the frangible coupling includes a frangible lattice web.

Example 14

The catheter system of any one or more of Examples 1 through 13, wherein the first guide segment is removably connected to the second guide segment by a threaded coupling for selective removal of the second guide segment from the first guide segment.

Example 15

The catheter system of any one or more of Examples 1 through 14, wherein the first guide segment is removably connected to the second guide segment by a slide coupling for selective removal of the second guide segment from the first guide segment, wherein the slide coupling includes a longitudinal rail extending from one of the first and second guide segments and a slot extending through a remaining one of the first and second guide segments, and wherein rail is configured to be slidably received within the slot.

Example 16

A guide catheter for a dilation catheter, comprising: (a) a shaft extending distally from the body and having a lumen extending longitudinally along a longitudinal axis, wherein the lumen is configured to movably receive the dilation catheter therein; and (b) a breakaway distal end portion having a conduit in communication with the lumen, wherein the conduit distally projects from the shaft and is configured to guide the dilation catheter at a first predetermined angle relative to the longitudinal axis and a second predetermined angle relative to the longitudinal axis for respectively dilating a first anatomy and a second anatomy, wherein the breakaway distal end portion includes: (i) a first guide segment at least partially defining the conduit and distally extending at the first predetermined angle to a first distal opening, and (ii) a second guide segment at least partially defining the conduit and distally extending from the first guide segment at the second predetermined angle to a second distal opening, wherein the second guide segment is removably connected to the first guide segment, wherein the first guide segment connected to the second guide segment are collectively configured to guide the dilation catheter through the second distal opening at the second predetermined angle for dilating the second anatomy, and wherein the first guide segment selectively disconnected from the second guide segment is configured to guide the dilation catheter through the first distal opening at the first predetermined angle for dilating the first anatomy.

Example 17

The guide catheter of Example 16, wherein the first guide segment is removably connected to the second guide segment by a frangible coupling for selective removal of the second guide segment from the first guide segment.

Example 18

The guide catheter of any one or more of Examples 16 through 17, wherein the first guide segment is removably connected to the second guide segment by a threaded coupling for selective removal of the second guide segment from the first guide segment.

Example 19

The guide catheter of any one or more of Examples 16 through 18, wherein the first guide segment is removably connected to the second guide segment by a slide coupling for selective removal of the second guide segment from the first guide segment, wherein the slide coupling includes a longitudinal rail extending from one of the first and second guide segments and a slot extending through a remaining one of the first and second guide segments, and wherein rail is configured to be slidably received within the slot.

Example 20

A method of dilating a first anatomical structure and a second anatomical structure with a catheter system, wherein the catheter system includes (a) a body; (b) a dilation catheter extending distally from the body and including an expandable dilator; and (c) a guide catheter including: (i) a shaft extending distally from the body and having a lumen extending longitudinally along a longitudinal axis, wherein the lumen movably receives the dilation catheter therein, and (ii) a breakaway distal end portion having a conduit in communication with the lumen, wherein the conduit distally projects from the shaft and is configured to guide the dilation catheter at a first predetermined angle relative to the longitudinal axis and a second predetermined angle relative to the longitudinal axis for respectively dilating the first and second anatomical structures, wherein the breakaway distal end portion includes: (A) a first guide segment at least partially defining the conduit and distally extending at the first predetermined angle to a first distal opening, and (B) a second guide segment at least partially defining the conduit and distally extending from the first guide segment at the second predetermined angle to a second distal opening, wherein the second guide segment is removably connected to the first guide segment, wherein the first guide segment connected to the second guide segment are collectively configured to guide the dilation catheter through the second distal opening at the second predetermined angle for dilating the second anatomical structure, and wherein the first guide segment selectively disconnected from the second guide segment is configured to guide the dilation catheter through the first distal opening at the first predetermined angle for dilating the first anatomical structure, the method comprising: (a) inserting the distal end portion into a patient's head; (b) advancing the dilation catheter relative to the guide catheter to thereby position the dilator along the second predefined angle and into the second anatomical structure, wherein the second anatomical structure is located in the patient's head; (c) expanding the dilator to thereby dilate the second anatomical structure; (d) removing the second guide segment from the first guide segment after the second anatomical structure has been dilated, thereby shortening an effective length of the distal end portion and providing the first predefined angle; (e) advancing the dilation catheter relative to the guide catheter to thereby position the dilator along the first predefined angle and into the first anatomical structure, wherein the first anatomical structure is located in the patient's head; and (f) expanding the dilator to thereby dilate the first anatomical structure.

Example 21

The method of Example 20, wherein the conduit of the breakaway distal end portion is further configured to guide the dilation catheter at a third predefined angle relative to the longitudinal axis for respectively dilating a third anatomy, wherein the breakaway distal end portion further includes a third guide segment at least partially defining the conduit and distally extending from the second guide segment at the third predefined angle to a third distal opening, wherein the third guide segment is removably connected to the second guide segment, and wherein the second guide segment connected to the third guide segment are collectively configured to guide the dilation catheter through the third distal opening at the third predefined angle for dilating the third anatomy the method including: (a) advancing the dilation catheter relative to the guide catheter to thereby position the dilator along the third predefined angle and into the third anatomical structure, wherein the third anatomical structure is located in the patient's head; (b) expanding the dilator to thereby dilate the third anatomical structure; and (c) removing the third guide segment from the second guide segment after the third anatomical structure has been dilated, thereby shortening the effective length of the distal end portion and providing the second predefined angle.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A catheter system, comprising:
   (a) a body;
   (b) a dilation catheter extending distally from the body and including an expandable dilator; and
   (c) a guide catheter including:
      (i) a shaft extending distally from the body and having a lumen extending longitudinally along a longitudinal axis, wherein the lumen movably receives the dilation catheter therein, and
      (ii) a breakaway distal end portion having a conduit in communication with the lumen, wherein the conduit distally projects from the shaft and is configured to guide the dilation catheter at an exit angle selected from a first predetermined angle relative to the longitudinal axis and a second predetermined angle relative to the longitudinal axis for respectively dilating a first anatomy and a second anatomy, wherein the breakaway distal end portion includes:
         (A) a first guide segment at least partially defining the conduit and distally extending at the first predetermined angle to a first distal opening such that the first guide segment is configured to guide the dilation catheter at the first predetermined angle as the dilation catheter is advanced distally through the first distal opening, and
         (B) a second guide segment at least partially defining the conduit and distally extending from the first guide segment at the second predetermined angle to a second distal opening such that the second guide segment is configured to guide the dilation catheter at the second predetermined angle as the dilation catheter is advanced distally through the second distal opening, wherein the second guide segment is removably connected to the first guide segment for adjustably selecting the exit angle from the first and second predetermined angles, wherein the first guide segment connected to the second guide segment are collectively configured to guide the dilation catheter through the second distal opening out of the conduit at the second predetermined angle for dilating the second anatomy, and wherein the first guide segment selectively disconnected from the second guide segment is configured to guide the dilation catheter through the first distal opening out of the conduit at the first predetermined angle for dilating the first anatomy, wherein the first predetermined angle is at least one of acute or obtuse.

2. The catheter system of claim 1, wherein the conduit of the breakaway distal end portion is further configured to guide the dilation catheter at a third predetermined angle relative to the longitudinal axis for respectively dilating a third anatomy, and wherein the breakaway distal end portion further includes a third guide segment at least partially defining the conduit and distally extending from the second guide segment at the third predetermined angle to a third distal opening, wherein the third guide segment is removably connected to the second guide segment, and wherein the second guide segment connected to the third guide segment are collectively configured to guide the dilation catheter through the third distal opening at the third predetermined angle for dilating the third anatomy.

3. The catheter system of claim 2, wherein the third, second, and first guide segments connected together are configured to guide the dilation catheter through the third distal opening at the third predetermined angle to dilate the third anatomy, wherein the third predetermined angle is between approximately 105 degrees and approximately 115 degrees, and wherein the third anatomy is a maxillary sinus ostium.

4. The catheter system of claim 3, wherein the second and first guide segments connected together are configured to guide the dilation catheter through the second distal opening at the second predetermined angle to dilate the second anatomy, wherein the second predetermined angle is between approximately 50 degrees and approximately 60 degrees, and wherein the second anatomy is a frontal recess.

5. The catheter system of claim 4, wherein the first guide segment is configured to guide the dilation catheter through the first distal opening at the first predetermined angle to dilate the first anatomy, and wherein the first anatomy is a sphenoid sinus ostium.

6. The catheter system of claim 1, wherein the second and first guide segments connected together are configured to guide the dilation catheter through the second distal opening at the second predetermined angle to dilate the second anatomy, wherein the second predetermined angle is between approximately 105 degrees and approximately 115 degrees, and wherein the second anatomy is a maxillary sinus ostium.

7. The catheter system of claim 6, wherein the first guide segment is configured to guide the dilation catheter through the first distal opening at the first predetermined angle to dilate the first anatomy, wherein the first predetermined angle is between approximately 50 degrees and approximately 60 degrees, and wherein the first anatomy is a frontal recess.

8. The catheter system of claim 1, wherein the second and first guide segments connected together are configured to guide the dilation catheter through the second distal opening at the second predetermined angle to dilate the second anatomy, wherein the second predetermined angle is between approximately 50 degrees and approximately 60 degrees, and wherein the second anatomy is a frontal recess.

9. The catheter system of claim 8, wherein the first guide segment is configured to guide the dilation catheter through the first distal opening at the first predetermined angle to dilate the first anatomy, and wherein the first anatomy is a sphenoid sinus ostium.

10. The catheter system of claim 1, wherein the first guide segment is removably connected to the second guide segment by a frangible coupling for selective removal of the second guide segment from the first guide segment.

11. The catheter system of claim 10, wherein the frangible coupling is configured to weaken upon exposure to at least one of heat or moisture.

12. The catheter system of claim 10, wherein the frangible coupling includes a scored portion.

13. The catheter system of claim 10, wherein the frangible coupling includes a frangible lattice web.

14. The catheter system of claim 1, wherein the first guide segment is removably connected to the second guide segment by a threaded coupling for selective removal of the second guide segment from the first guide segment.

15. The catheter system of claim 1, wherein the first guide segment is removably connected to the second guide segment by a slide coupling for selective removal of the second guide segment from the first guide segment, wherein the slide coupling includes a longitudinal rail extending from one of the first and second guide segments and a slot extending through a remaining one of the first and second guide segments, and wherein the rail is configured to be slidably received within the slot.

16. A guide catheter for a dilation catheter, comprising:
(a) a shaft having a lumen extending longitudinally along a longitudinal axis, wherein the lumen is configured to movably receive the dilation catheter therein; and
(b) a breakaway distal end portion having a conduit in communication with the lumen, wherein the conduit distally projects from the shaft and is configured to guide the dilation catheter at an exit angle selected from a first predetermined angle relative to the longitudinal axis and a second predetermined angle relative to the longitudinal axis for respectively dilating a first anatomy and a second anatomy, wherein the breakaway distal end portion includes:
(i) a first guide segment at least partially defining the conduit and distally extending at the first predetermined angle to a first distal opening such that the first guide segment is configured to guide the dilation catheter at the first predetermined angle as the dilation catheter is advanced distally through the first distal opening, and
(ii) a second guide segment at least partially defining the conduit and distally extending from the first guide segment at the second predetermined angle to a second distal opening such that the second guide segment is configured to guide the dilation catheter at the second predetermined angle as the dilation catheter is advanced distally through the second distal opening, wherein the second guide segment is removably connected to the first guide segment for adjustably selecting the exit angle from the first and second predetermined angles,
wherein the first guide segment connected to the second guide segment are collectively configured to guide the dilation catheter through the second distal opening out of the conduit at the second predetermined angle for dilating the second anatomy, and
wherein the first guide segment selectively disconnected from the second guide segment is configured to guide the dilation catheter through the first distal opening out of the conduit at the first predetermined angle for dilating the first anatomy,
wherein the first guide segment includes a preformed bend.

17. The guide catheter of claim 16, wherein the first guide segment is removably connected to the second guide segment by a frangible coupling for selective removal of the second guide segment from the first guide segment.

18. The guide catheter of claim 16, wherein the first guide segment is removably connected to the second guide segment by a threaded coupling for selective removal of the second guide segment from the first guide segment.

19. The guide catheter of claim 16, wherein the first guide segment is removably connected to the second guide segment by a slide coupling for selective removal of the second guide segment from the first guide segment, wherein the slide coupling includes a longitudinal rail extending from one of the first and second guide segments and a slot extending through a remaining one of the first and second guide segments, and wherein the rail is configured to be slidably received within the slot.

20. A method of dilating a first anatomical structure and a second anatomical structure with a catheter system, wherein the catheter system includes (a) a body; (b) a dilation catheter extending distally from the body and including an expandable dilator; and (c) a guide catheter including: (i) a shaft extending distally from the body and having a lumen extending longitudinally along a longitudinal axis, wherein the lumen movably receives the dilation catheter therein, and (ii) a breakaway distal end portion having a conduit in communication with the lumen, wherein the conduit distally projects from the shaft and is configured to guide the dilation catheter at a first predefined angle relative to the longitudinal axis and a second predefined angle relative to the longitudinal axis for respectively dilating the first and second anatomical structures, wherein the breakaway distal end portion includes: (A) a first guide segment at least partially defining the conduit and distally extending at the first predefined angle to a first distal opening, and (B) a second guide segment at least partially defining the conduit and distally extending from the first guide segment at the second predefined angle to a second distal opening, wherein the second guide segment is removably connected to the first guide segment, wherein the first guide segment connected to the second guide segment are collectively configured to guide the dilation catheter through the second distal opening at the second predefined angle for dilating the second anatomical structure, and wherein the first guide segment selectively disconnected from the second guide segment is configured to guide the dilation catheter through the first distal opening at the first predefined angle for dilating the first anatomical structure, the method comprising:
(a) inserting the distal end portion into a patient's head;
(b) advancing the dilation catheter relative to the guide catheter to thereby position the dilator along the second predefined angle and into the second anatomical structure, wherein the second anatomical structure is located in the patient's head;
(c) expanding the dilator to thereby dilate the second anatomical structure;
(d) removing the second guide segment from the first guide segment after the second anatomical structure has been dilated, thereby shortening an effective length of the distal end portion and providing the first predefined angle;

(e) advancing the dilation catheter relative to the guide catheter to thereby position the dilator along the first predefined angle and into the first anatomical structure, wherein the first anatomical structure is located in the patient's head; and (f) expanding the dilator to thereby dilate the first anatomical structure.

* * * * *